United States Patent
Sahay et al.

[11] Patent Number: 5,824,085
[45] Date of Patent: Oct. 20, 1998

[54] SYSTEM AND METHOD FOR CAVITY GENERATION FOR SURGICAL PLANNING AND INITIAL PLACEMENT OF A BONE PROSTHESIS

[75] Inventors: Alind Sahay, Sacramento; Brent Mittelstadt, Placerville; Willie Williamson, Jr., Roseville; Joel Zuhars; Peter Kazanzides, both of Sacramento, all of Calif.

[73] Assignee: Integrated Surgical Systems, Inc., Sacramento, Calif.

[21] Appl. No.: 724,497

[22] Filed: Sep. 30, 1996

[51] Int. Cl.⁶ .................................................. A61F 2/28
[52] U.S. Cl. .............................. 623/16; 623/22; 606/53; 606/86; 606/79; 395/80
[58] Field of Search .................. 606/79, 80, 86, 606/89; 623/16, 22, 23, 66; 128/898, 920, 922, 923; 364/413.13; 395/80, 924

[56] References Cited

U.S. PATENT DOCUMENTS

| | | | |
|---|---|---|---|
| 5,086,401 | 2/1992 | Glassman et al. | 395/94 |
| 5,299,288 | 3/1994 | Glassman et al. | 395/80 |
| 5,408,409 | 4/1995 | Glassman et al. | 364/413.3 |

OTHER PUBLICATIONS

Mittelstadt et al., "Development of a surgical robot for cementless total hip replacement", Robotica (1993) vol. 11, pp. 553–560, Mar. 1993.

*Primary Examiner*—Michael Powell Buiz
*Assistant Examiner*—David O. Reip
*Attorney, Agent, or Firm*—Townsend and Townsend and Crew LLP

[57] ABSTRACT

Methods, systems and apparatus for planning the position of a prosthesis in a long bone in orthopaedic surgical procedures, such as hip replacement surgery, knee replacement surgery, long bone osteotomies, and the like. A bone model is generated from a scanned image of a bone, a prosthesis model is selected from a library of prosthesis models and then a cavity model is formed based on the prosthesis model and/or the bone model. The cavity model may then be positioned over the bone model, either interactively by the surgeon or automatically through an algorithm based on clinical parameters, to determine a reasonable location for implantation of a prosthesis within the bone. The cavity model allows the surgeon to optimize placement of the implant within the bone, and it provides important clinical information to the surgeon, such as areas in which press fits are provided, extension areas for possible subsidence and access areas for allowing the surgeon to insert the implant into the cavity.

30 Claims, 13 Drawing Sheets

SYSTEM AND METHOD FOR CAVITY GENERATION FOR SURGICAL PLANNING AND INITIAL PLACEMENT OF A BONE PROSTHESIS

COPYRIGHT NOTICE

A portion of the disclosure of this patent document contains material which is subject to copyright protection. The copyright owner has no objection to the xerographic reproduction by anyone of the patent document(s) or the patent disclosure in exactly the form it appears in the Patent and Trademark Office patent file or records, but otherwise reserves all copyrights whatsoever.

BACKGROUND OF THE INVENTION

CROSS-REFERENCE TO RELATED APPLICATIONS

The disclosure of the present patent application is related to copending U.S. patent application Ser. No. 08/526,826, filed on Sep. 11, 1995, and to U.S. patent application Ser. No. 08/606,989, filed on Feb. 22, 1996, the full disclosures of which are incorporated herein by reference. The disclosure of the present application is further related to application Ser. No. 08/720,544 (Attorney Docket No. 17150-000700US), filed on the same date as the present application, the full disclosure of which is incorporated herein by reference.

1. Field of the Invention

The present invention relates to surgical systems and methods for implanting bone prostheses. More specifically, the present invention provides a system and method for planning the position of a prosthesis within a long bone, such as the femur, tibia, humerus, ulna, and radius, with specific procedures including total hip joint replacement, knee joint replacement, long bone osteotomy, and the like.

Total hip replacement (THR) surgery (also called primary total hip arthroplasty) is a surgical procedure where a surgeon replaces a patient's ball-and-socket joint with a prosthetic device. The prosthetic device includes an acetabular cup and a femoral prosthesis. The femoral prosthesis provides the replacement "ball" and the acetabular cup provides the replacement "socket" of the ball-and-socket joint. The femoral prosthesis includes a femoral head and a femoral stem. The surgeon implants the femoral prosthesis by first removing the bone femoral head and then excavating to and extending the femoral canal within the femur so that the femoral stem may be placed in the femoral canal adjacent to the cortical bone. Once the femoral prosthesis is implanted, the femoral head of the prosthesis is adjacent to the trabecular bone.

Surgeons typically prepare a cavity for the femoral stem with inaccurate methods. Reamers (hand-held drills) and broaches (serrated cutting tools) are utilized by surgeons to produce the femoral cavity. Laboratory tests have shown that the cavities produced by these methods are irregular, resulting in relatively large gaps between the bone and the prosthesis. These gaps may result when the broach tears out chunks of trabecular bone instead of making a precise cut. Additionally, the gaps may be caused by the tendency of a broach to cut the material with the least resistance when it makes contact with dense trabecular or cortical bone. Bone cement (polymethylmethacrylate or PMMA) is typically utilized to fill in the gaps between the femur and the femoral prosthesis.

Robotic systems for assisting in a number of medical procedures have been proposed, including neurosurgical, laparoscopic, and orthopedic procedures. While the details of a particular procedure may vary widely, a number of such procedures rely on first obtaining a preoperative image of the region to be operated on, and subsequently robotically controlling a medical tool based on information in the preoperative image. Of particular interest to the present invention, robotically assisted total hip replacement surgery is performed by first imaging the femur, typically by computerized tomography (CT), and producing a digital data set representative of the femur. Selection and positioning of an implant within the femur is then planned at a computer workstation, such as the ORTHODOCT™ presurgical planning workstation being developed by Integrated Surgical Systems, Inc., Sacramento, Calif., assignee of the present application. Once the doctor has planned the implant placement on the workstation, a digital data set including both the image data (patient anatomy) and the planned positioning of the implant is produced. It is then necessary to transfer this data set to a computer-controlled robotic system intended to perform the surgery, such as the ROBODOC™ surgical robot system which is also being developed by Integrated Surgical Systems.

An important consideration in planning an implant placement for a long bone is the selection of a suitable prosthesis for the particular bone cavity, and positioning the selected prothesis in the appropriate location within the femur bone. Currently, this process involves generating a scanned image of the bone and selecting a prosthesis from a library of existing prostheses based on this image. During the surgical procedure, the surgeon cuts a cavity within the bone based on the selected prosthesis, and inserts the prosthesis manually or automatically into the bone cavity. The actual cavity that is formed during the procedure, however, will usually have a different size and shape than the prosthesis. For example, the cavity generally includes access areas proximal to the intended location of the prosthesis to facilitate implantation of the prosthesis into the cavity. The surgeon may also desire to include extension areas within the cavity to accommodate subsidence of the prosthesis. In addition, the surgeon may desire to optimize the cavity for a particular patient. For example, it may be desirable to individually optimize the interference fit between the implant and the bone, the loading of the implant, the stress transfer from implant to bone, and other clinical factors.

For these and other reasons, it would be desirable to provide improved methods in robotic systems for performing surgical procedures on long bones, such as joint replacement procedures on femurs and other long bones. It would be particularly desirable to provide methods and systems that allow the surgeon to plan the actual cavity that will be formed in the bone to optimize selection and placement of the prosthesis.

2. Description of the Background Art

Conventional techniques for bone cement removal in revision total hip replacement surgery are described in Lombardi, Jr., A.: "Cement Removal in Revision Total Hip Arthroplasty," *Seminars in Arthroplasty*, Volume 3, No. 4, Pages 264–272, October 1992.

The ORTHODOC™ presurgical planning workstation and the ROBODOC™ robotic surgical system are described in a number of references, including the following: Kazanzides, P., Zuhars, J., Mittelstadt, B. D., Taylor, R. H.: "Force Sensing and Control for a Surgical Robot," *Proc. IEEE Conference. on Robotics & Automation*, Pages 612–616, Nice, France, May 1992. Kazanzides, P., Zuhars, J., Mittelstadt, B. D., Williamson, B., Cain, P., Smith, F., Rose, L., Mustis, B.: "Architecture of a Surgical Robot," *Proc. IEEE Conference. on Systems, Man, and Cybernetics*, Chicago, Ill., Pages 1624–1629, October, 1992. Paul, H. A., Bargar, W. L., Mittelstadt, B., Musits, B., Taylor, R. H., Kazanzides, P., Zuhars, J., Williamson, B., Hanson, W.: "Development of a Surgical Robot For Cementless Total Hip Arthroplasty," *Clinical Orthopaedics*, Volume 285, Pages 57–66, December 1992. Kazanzides, P., Mittelstadt, B. D., Zuhars, J., Cain, P., Paul, H. A., "Surgical and Industrial Robots: Comparison and Case Study," *Proc. International Robots and Vision Automation Conference*, Pages 1019–1026, Detroit, Mich., April 1993. Mittelstadt, B., Kazanzides, P., Zuhars, J., Williamson, B., Pettit, R., Cain, P., Kloth, D., Rose, L., Musits, B.: "Development of a surgical robot for cementless total hip replacement," *Robotica*, Volume 11, Pages 553–560, 1993. Mittelstadt B., Kazanzides, P., Zuhars, J., Cain, P., Williamson, B.: "Robotic surgery: Achieving predictable results in an unpredictable environment," *Proc. Sixth International Conference on Advanced Robotics*, Pages 367–372, Tokyo, November, 1993. Cain, P., Kazanzides, P., Zuhars, J., Mittelstadt, B., Paul, H.: "Safety Considerations in a Surgical Robot," *Biomedical Sciences Instrumentation*, Volume 29, Pages 291–294, San Antonio, Tex., April 1993. Mittelstadt, B. D., Kazanzides, P., Zuhars, J., Williamson, B., Cain, P., Smith, F. Bargar, W.: "The Evolution of A Surgical Robot From Prototype to Human Clinical Use," *in Proc. First International Symposium on Medical Robotics and Computer Assisted Surgery*, Volume I, Pages 36–41, Pittsburgh, Pa., September 1994.

Other publications which describe image registration in robotic surgical and other procedures include the following: Grimson, W. E. L., Lozano-Pérez, T., Wells III, W. M., Ettinger, G. J., White, S. J., Kikinis, R.: "Automated Registration for Enhanced Reality Visualization in Surgery," *Proceedings of the First International Symposium on Medical Robotics and Computer Assisted Surgery*, Volume I, Sessions I–III, Pages 82–89, Pittsburgh, Pa., Sep. 22–24, 1995. Nolte, L. P., Zamorano, L. J., Jiang, Z., Wang, Q., Langlotz, F., Arm, E., Visarius, H.: "A Novel Approach to Computer Assisted Spine Surgery," *Proceedings of the First International Symposium on Medical Robotics and Computer Assisted Surgery*, Volume II, Session IV, Pages 323–328, Pittsburgh, Pa., Sep. 22–24, 1994. Lavallée, S., Sautot, P., Troccaz, J., Cinquin, P., Merloz, P.: "Computer Assisted Spine Surgery: a technique for accurate transpedicular screw fixation using CT data and a 3-D optical localizer," *Proceedings of the First International Symposium on Medical Robotics and Computer Assisted Surgery*, Volume II, Session IV, Pages 315–321, Pittsburgh, Pa., Sep. 22–24, 1994. Potamianos, P., Davies, B. L., Hibberd, R. D.: "Intra-Operative Imaging Guidance For Keyhole Surgery Methodology and Calibration," *Proceedings of the First International Symposium on Medical Robotics and Computer Assisted Surgery*, Volume I, Sessions I–III, Pages 98–104, Pittsburgh, Pa., Sep. 22–24, 1994. Simon, D. A., Hebert, M., Kanade, T.: "Techniques for Fast and Accurate Intra-Surgical Registration," *Proceedings of the First International Symposium on Medical Robotics and Computer Assisted Surgery*, Volume I, Sessions I–III, Pages 90–97, Pittsburgh, Pa., Sep. 22–24, 1995. Péria, O., François-Joubert, A., Lavallée, S., Champleboux, G., Cinquin, P., Grand, S.: "Accurate Registration of SPECT and MR brain images of patients suffering from epilepsy or tumor," *Proceedings of the First International Symposium on Medical Robotics and Computer Assisted Surgery*, Volume II, Session IV, Pages 58–62, Pittsburgh, Pa., Sep. 22–24, 1995. Lea, J. T., Watkins, D., Mills, A., Peshkin, M. A., Kienzle III, T. C., Stulberg, D. S.: "Registration and Immobilization for Robot-Assisted Orthopaedic Surgery," *Proceedings of the First International Symposium on Medical Robotics and Computer Assisted Surgery*, Volume I, Sessions I–III, Pages 63–68, Pittsburgh, Pa., Sep. 22–24, 1995. Ault, T., Siegel, M. W.: "Frameless Patient Registration Using Ultrasonic Imaging," *Proceedings of the First International Symposium on Medical Robotics and Computer Assisted Surgery*, Volume I, Sessions I–III, Pages 74–81, Pittsburgh, Pa., Sep. 22–24, 1995. Champleboux, G., Lavallée, S., Cinquin, P.: "An Optical Conformer for Radiotherapy Treatment Planning," *Proceedings of the First International Symposium on Medical Robotics and Computer Assisted Surgery*, Volume I, Sessions I–III, Pages 69–73, Pittsburgh, Pa., Sep. 22–24, 1995.

A system and method for performing robotically assisted surgery is described in U.S. Pat. No. 5,086,401. Computer-assisted imaging and probe tracking systems are described in U.S. Pat. No. 5,383,454; U.S. Pat. No. 5,198,877; and WO 91/07726.

SUMMARY OF THE INVENTION

The present invention provides improved methods, systems and apparatus for planning the position of a prosthesis in a bone in orthopaedic surgical procedures. The present invention is particularly useful for planning the implantation of a long bone prosthesis, such as hip replacement surgery, knee replacement surgery, long bone osteotomies, and the like. The method of the present invention generally includes the steps of generating a model of the long bone, creating a prosthesis model and generating a cavity model based on the prosthesis model. The prosthesis model may be selected from a library or database of existing prostheses, or it may be individually tailored for the patient. The bone model is usually generated from a scanned image of the bone, such as computerized tomography (CT), digital radiography, or the like. The cavity model is typically generated by a set of rules which create cavity dimensions based on prothesis model information and/or bone model information. The cavity model may then be positioned over the bone model, either interactively by the surgeon or automatically through an algorithm based on clinical parameters, to determine a reasonable location for implantation of a prosthesis within the bone.

The methods, systems and apparatus of the present invention are particularly advantageous since they allow the surgeon to generate a model of the actual cavity that will be formed during implantation to optimize placement of the implant within the bone. The cavity model provides important clinical information to the surgeon, such as areas in which press fits are provided, extension areas for possible subsidence and access areas for allowing the surgeon to insert the implant into the cavity. Providing a cavity model also allows the surgeon to examine individual axial cross sections of the bone to manually optimize the placement of the implant. In addition, the surgeon may determine the amount of extension area that should be removed, and position the implant so that a minimum amount of cortical bone is removed distally of the planned implant location. The surgeon may also monitor the robot axis path in the access region and plan for the robot axis path during surgery to minimize the amount of time spent by the robotic cutter in the air.

In a specific aspect of the invention, a first cavity model includes an access region, a proximal cavity region, a distal cavity region and a distal extension region. The access region is an area above the proximal portion of the prosthesis (after it has been implanted into the bone) that typically must be removed to provide access to the actual cavity in which the prothesis will be implanted. The proximal cavity region generally refers to the proximal portion of the cavity that is wider in the lateral/medial direction than the remainder of the cavity to accommodate the proximal portion of the prosthesis model. The distal cavity region is usually more narrow in the lateral/medial direction than the proximal cavity region to accommodate the distal portion of the prothesis model, and to provide a relatively tight interference fit with the prothesis model and the cortical bone. The distal extension cavity is the portion of the cavity that extends beyond the distal point of the prothesis model to provide room for subsidence of the implant after it has been deployed within the cavity. In an exemplary embodiment, the distal extension cavity is optimized based on the thickness of the cortical bone and the predicted metaphyseal contact between the bone and the prothesis.

In another aspect of the invention, the cavity model is positioned over the bone model to determine a range of potential implant sizes and initial placement of the prosthesis at a reasonable location within the bone cavity. In one embodiment, the cavity model is positioned interactively by observing images of the bone model and the cavity model on a display, and adjusting the image of the bone model relative to the cavity model as they appear on the display. In another embodiment, this positioning is accomplished automatically with an algorithm based on measurements of the bone model and clinical parameters. The clinical parameters may, for example, include prosthesis fit criteria for determining potential implant sizes and locations. In a preferred configuration, the algorithm includes selecting a group of implants and determining a quantitative valve for each implant within the group based on the fit criteria. Exemplary fit criteria include minimizing the amount of cortical bone that is removed, maximizing contact between selected portions of the implant and the bone and minimizing gaps between the bone and selected portions of the implant.

Once the initial cavity model has been generated, this model can be adjusted based on the patient's individual requirements. For example, the quality or hardness of the patient's bone typically affects the interference fit between the prosthesis and the bone. Preferably, the dimensions of the first cavity model are adjusted to produce a second cavity model. The second cavity model is then repositioned either automatically (i.e., by an algorithm similar to that described previously for the first cavity model) or interactively by observing images of the bone model and the second cavity model on the display and adjusting the relative positions of the images as they appear on the display.

Other features and advantages of the present invention will become readily apparent upon a perusal of the following description and accompanying drawings.

DETAILED DESCRIPTION OF THE SPECIFIC EMBODIMENTS

Figure 1:
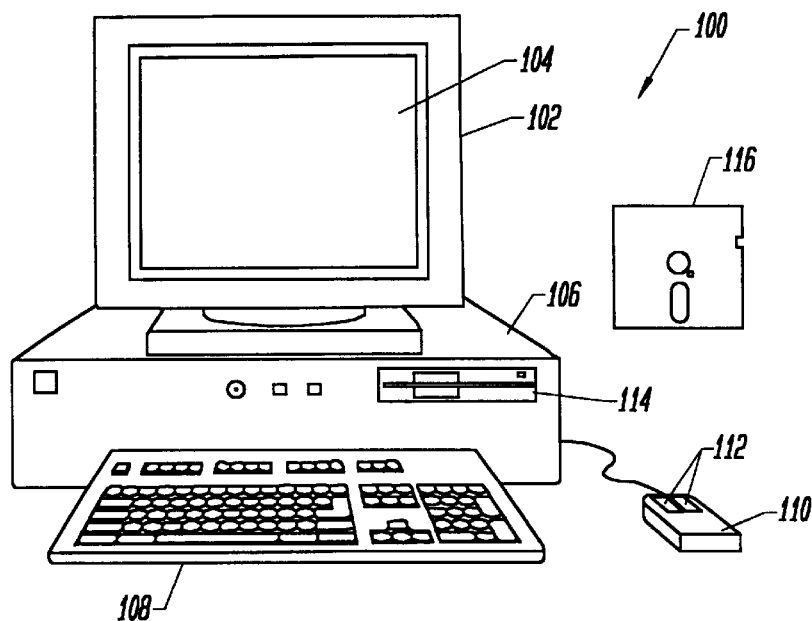
FIG. 1 illustrates an example of a computer system capable of executing the software of the present invention.

The present invention provides systems and methods for planning the position of a prosthesis within a bone. The present invention is particularly useful in planning the implantation of a prosthesis in a long bone, such as the femur, tibia, humerus, ulna, and radius. Planning the position of a prosthesis in such long bones will be particularly useful in conjunction with robotic surgical procedures, such as joint replacement, with specific procedures including total hip joint replacement, knee joint replacement, long bone osteotomy, and the like. The present invention, however, is not limited to such robotic procedures and will be equally useful in manual surgical, diagnostic, and other medical procedures where it is necessary to align a pre-obtained image of a long bone within an actual coordinate space, such as an operative space. Such manual systems and procedures include computer-assisted surgical procedures that employ optical surgical measurement tools, passive electromechanical devices, and the like.

The method of the present invention generally includes the steps of generating a bone model from a scanned image of a bone, creating a prosthesis model, generating a cavity model based on the prosthesis model and/or the bone model, and positioning the cavity model within the bone model. The cavity model may be created from the prosthesis model alone, or from information obtained from both the prosthesis and bone models. The bone model is a geometric model which contains enough information to define the inner and outer bounding surfaces of the bone. Common techniques for creating such a model are the "marching cubes" algorithm and the contour based method. W. E. Lorensen and H. E. Cline "Marching Cubes: A High Resolution 3D Surface Construction Algorithm" *Computer Graphics*, 21(4), (1987).

The prosthesis model is usually selected from a library or database of implant designs of different femoral prostheses, which may be stored on a suitable tangible medium, such as a floppy disk. The implant designs are typically in the form of computer aided design (CAD) models which may be available from the manufacturers. Alternatively, the surgeon may create a prothesis model that is individually customized for the patient.

The present invention relies on obtaining an image of the bone using a conventional medical imaging technique, such as computerized tomography (CT), radiography (digitized X-ray images), magnetic resonance imaging (MRI), and the like. Usually, CT and radiographic imaging will be preferred since they provide particularly accurate imaging information of bone material. In all cases, the image will be obtained in or converted to a digital form to produce an image data set which is suitable for digital manipulation using conventional computerized image processing equipment and software. Usually, the image processing equipment will be in the form of specially programmed computers, which are generally referred to as controllers and processors hereinafter. In particular, the present invention will utilize a preoperative planning work station (computer) for analyzing and manipulating raw image data which is obtained directly from the image itself.

Figure 2:
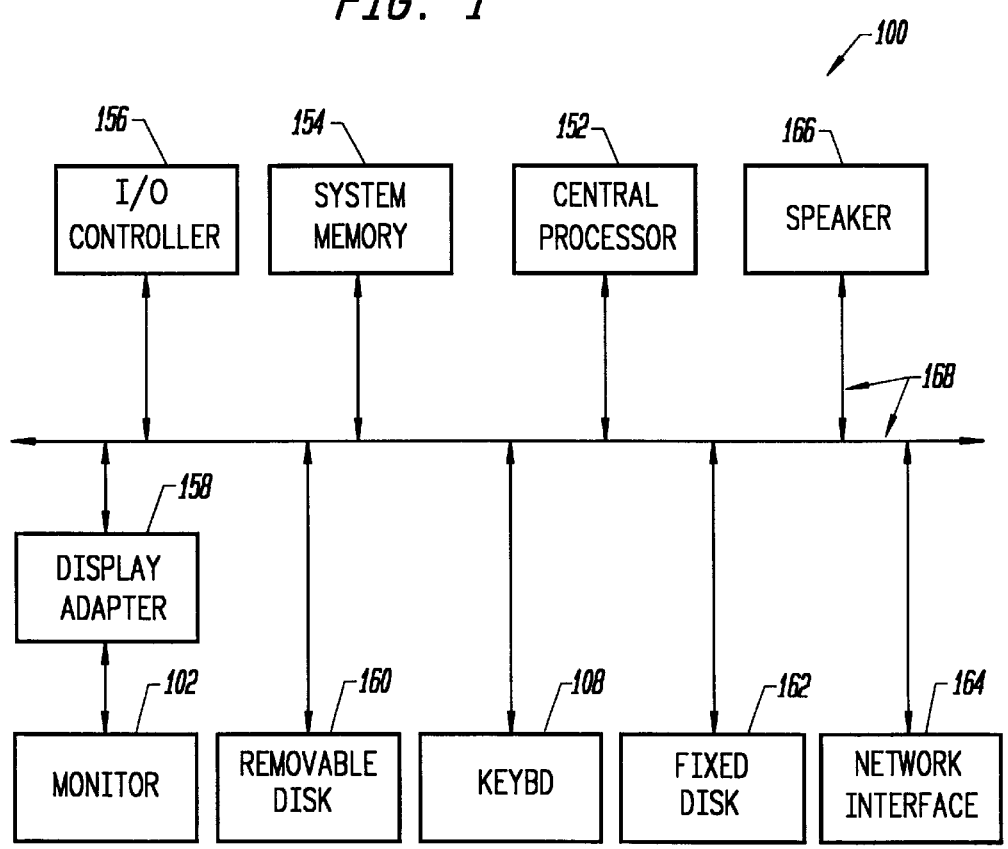
FIG. 2 shows a system block diagram of a typical computer system.

FIG. 1 illustrates an example of a computer system capable of executing the software of the present invention. FIG. 2 shows a computer system 100 which includes a monitor 102, display screen 104, cabinet 106, keyboard 108, and mouse 110. Mouse 110 may have one or more buttons such as mouse buttons 112. Cabinet 106 houses a floppy drive 114 or a hard drive (not shown) which may be utilized to store and retrieve the computer readable code of software programs incorporating the present invention, patient information, image data of bones, files defining cutting contours, and the like. Although a floppy diskette 116 is shown as the removable media, other removable tangible media including CD-ROM, tape, and flash memory may be utilized. Cabinet 106 also houses familiar computer components (not shown) such as a processor, memory, and the like.

FIG. 2 shows a system block diagram of computer system 100. As in FIG. 2, computer system 100 includes monitor 102 and keyboard 108. Computer system 100 further includes subsystems such as a central processor 152, system memory 154, I/O controller 156, display adapter 158, removable disk 160, fixed disk 162, network interface 164, and speaker 166. Other computer systems suitable for use with the present invention may include additional or fewer subsystems. For example, another computer system could include more than one processor 102 (i.e., a multi-processor system) or a cache memory.

Figure 3:
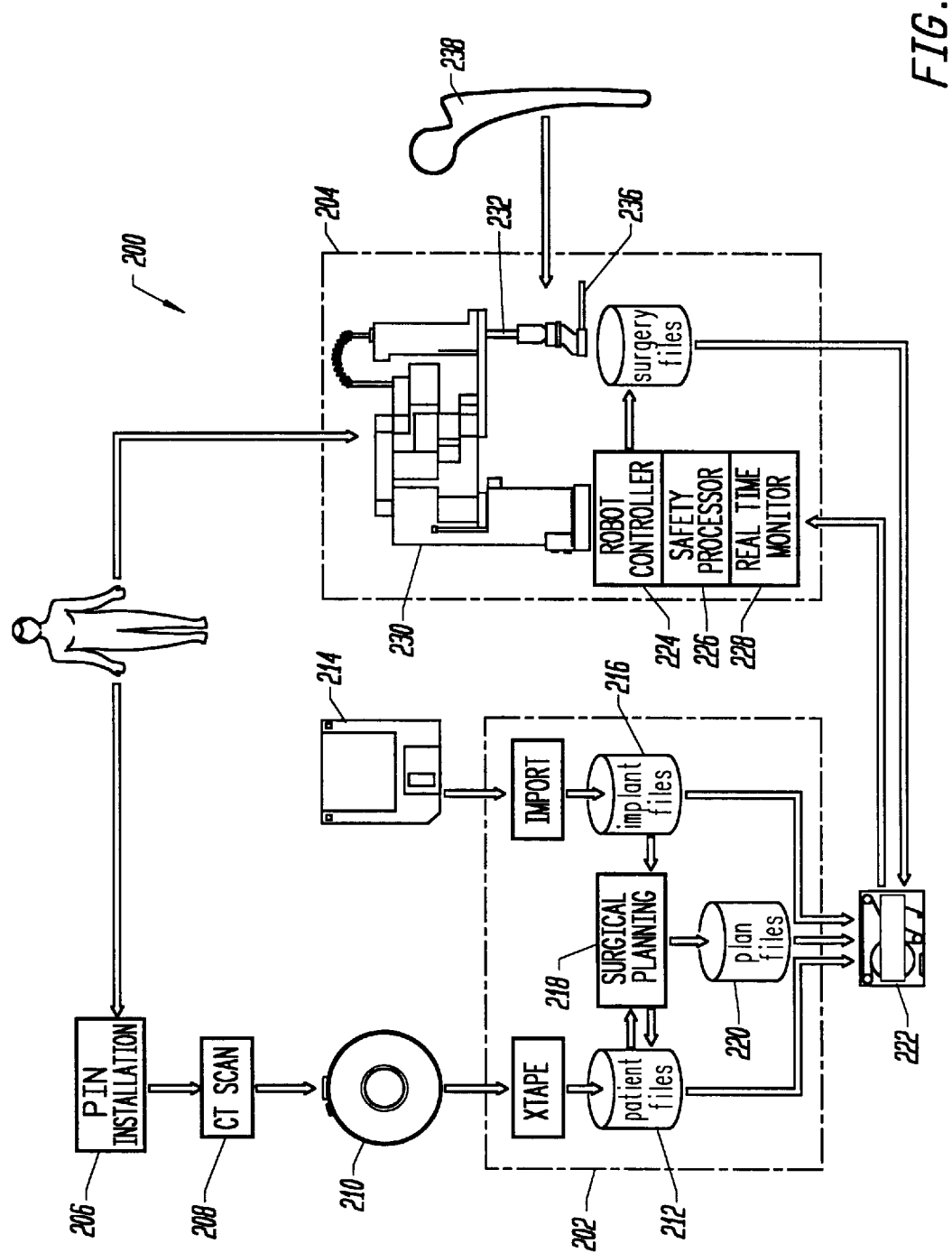
FIG. 3 illustrates an architecture of a robotic surgical system including a presurgical planning component and a surgical component.

Arrows such as 168 represent the system bus architecture of computer system 100. However, these arrows are illustrative of any interconnection scheme serving to link the subsystems. For example, a local bus could be utilized to connect the central processor to the system memory and display adapter. Computer system 100 shown in FIG. 3 is but an example of a computer system suitable for use with the present invention. Other configurations of subsystems suitable for use with the present invention will be readily apparent to one of ordinary skill in the art.

In a preferred embodiment, the present invention operates on an IBM RS/6000 computer running the UNIX operating system. However, the invention is not limited to any computer architecture or operating system and the description of the embodiments that follows is for purposes of illustration and not limitation.

FIG. 3 illustrates an architecture of a robotic surgical system including a presurgical planning component and a surgical component which are capable of implementing the methods of the present invention. A system 200 for revision total hip replacement surgery may include both a presurgical planning workstation 202 and a surgical robot system 204. In a preferred embodiment, the presurgical planning workstation is the ORTHODOC™ presurgical planning workstation which includes an IBM RS/6000 computer. In a preferred embodiment, the surgical robot system is the ROBODOC™ surgical robot system. The following will describe the present invention in reference to a preferred embodiment utilizing the ORTHODOC™ presurgical planning workstation and the ROBODOC™ surgical robot system. However, other systems may be utilized and therefore this description is for purposes of illustration and not limitation.

For alignment of the femur, the surgical robot system relies on the surgical implantation of a pair of metallic pins on the distal (lower) end of the femur and one additional metallic pin in the proximal end of the bone. These pins are readily apparent in the CT image of the bone and can thus be relied on to register the bone image with the robotic coordinate space by engaging a probe placed on the manipulator arm against each of the pins. Accordingly, prior to surgery, pin installation 206 will be performed followed by a CT scan 208. The image data from the CT scan is stored on a magnetic tape 210. Presurgical planning workstation 202 reads the CT scan data and stores it in a database of patient files 212. Although the present invention will be described as utilizing a CT scan, other imaging techniques may be utilized including x-rays.

Implant designs of different femoral prostheses may be stored on a floppy disk 214. The implant designs are typically in the form of faceted surface models, which are processed from computer aided design (CAD) models which may be available from the manufacturers. Presurgical planning workstation 202 reads the implant designs and stores them in a database of implant files 216. The presurgical planning workstation utilizes data from the patient files and implant files to allow a surgeon to perform surgical planning 218 of the revision total hip replacement. Details of the surgical planning will be described in more detail below. Surgical planning generates plan files 220 which may include a cut binary file and a check volume file. The plan files may be placed on a digital tape 222 for use by the surgical robot system.

Surgical robot system 204 includes a robotic controller 224 (typically a digital processor in the form of a programmable computer), a safety processor 226, a real time monitor computer 228, and a robot 230. The robot can be any conventional industrial robot having a manipulatable arm 232 preferably having at least 5 axes and capable of high precision placement. A suitable robotic is available from Sankyo Robotics with the model designation SR-5427-ISS. For use in the present invention, a force sensor 234 is mounted at the distal end of arm 232, and an effector in the form of a probe 236 or a surgical cutting tool (not shown) may be attached to the force sensor to cut a cavity for a femoral prosthesis 238.

The surgical robot system further includes a display monitor and a bone motion monitor (both not shown). The force sensor, safety processor, real time monitor, and bone motion monitor, each help monitor the position, slippage, and blockage of the effector end of the manipulatable arm 232 while the femur is held in place in a fixator assembly (not shown). Real time monitoring of these parameters helps assure that the robotic system is operating as planned. Details of these monitoring systems are described in the literature cited above which describes the ROBODOC™ robotic surgical system.

Figure 4:
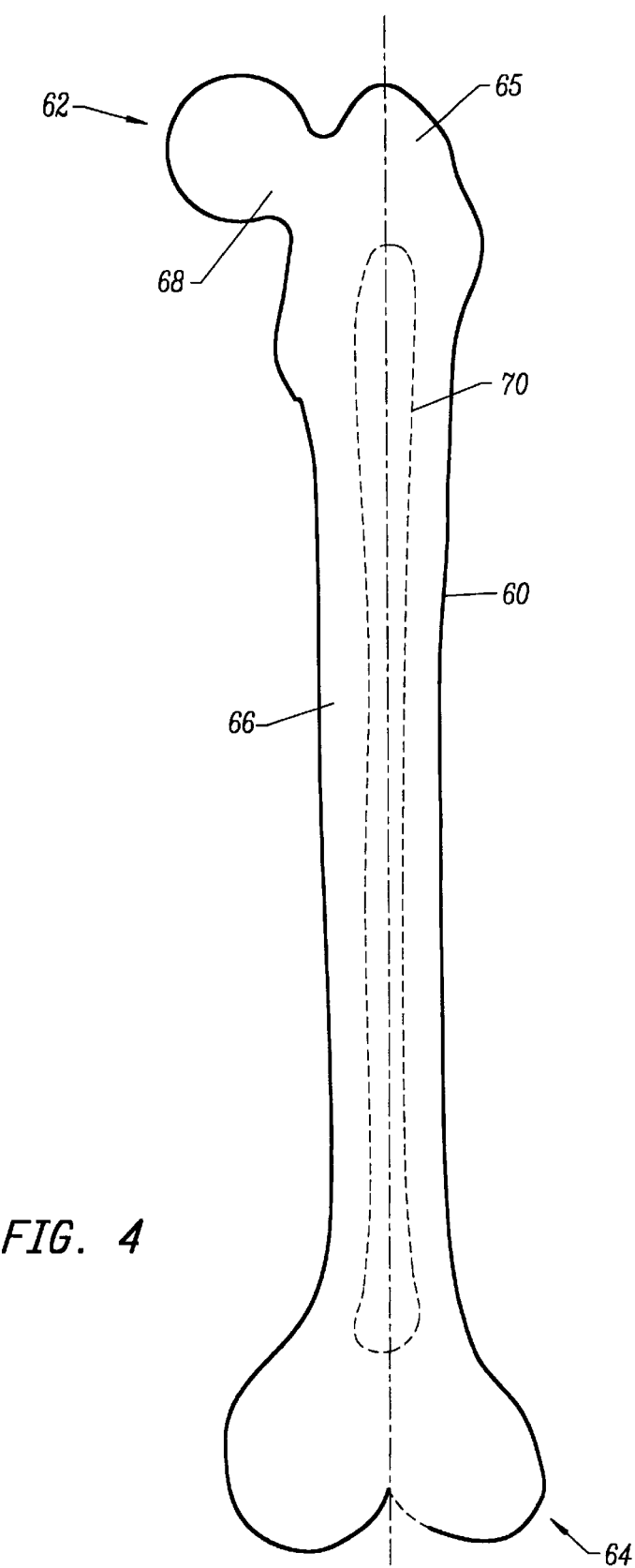
FIG. 4 is a schematic illustration of a human femur.
Figure 5:
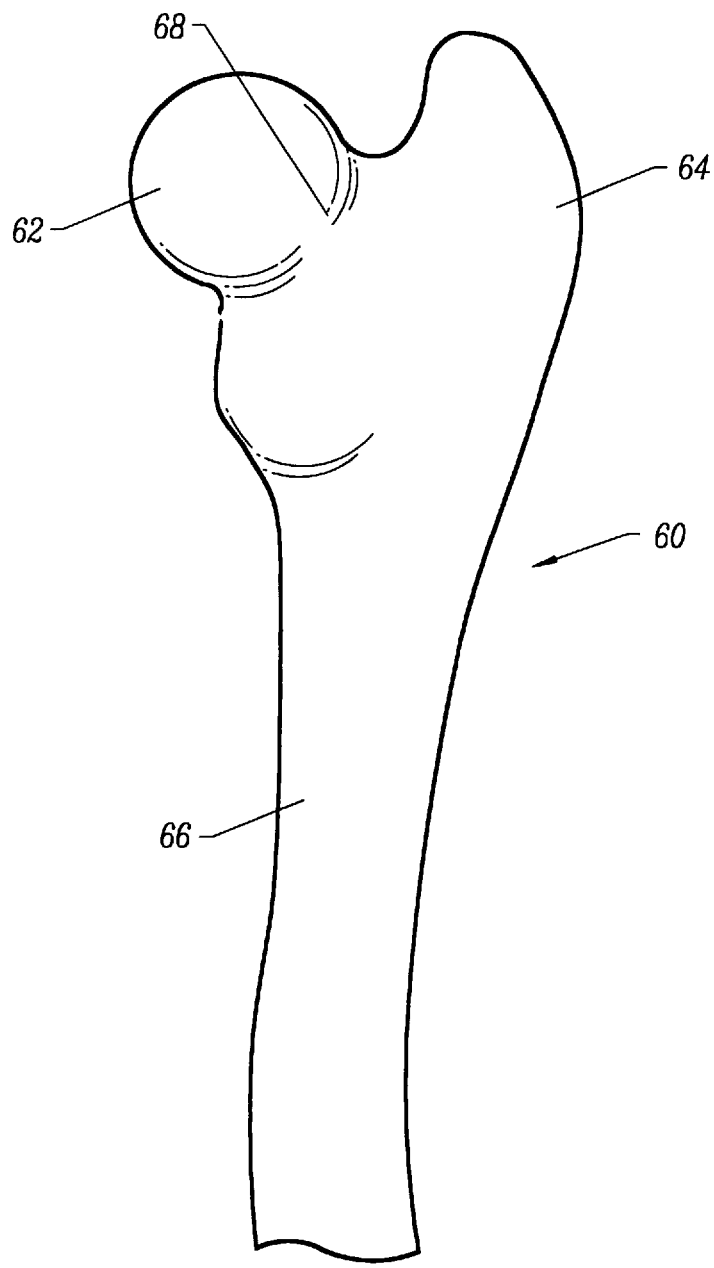
FIG. 5 is a detailed view of the upper end of a human femur.

Before describing the method of the present invention in detail, it is necessary to describe the physical characteristics of the femur, a typical long bone. Referring now to FIGS. 4 and 5, a femur 60 comprises a head region 62 and a lower region 64. The trabecular bone 65 that is located adjacent the femoral head 62 and the cortical bone is located generally between the two ends of the bone. A neck region 68 is located just below the femoral head above the trabecular bone. Finally, the medullary canal 70 runs generally axially through the cortical bone region of the femur, as shown in broken line.

Figure 6:
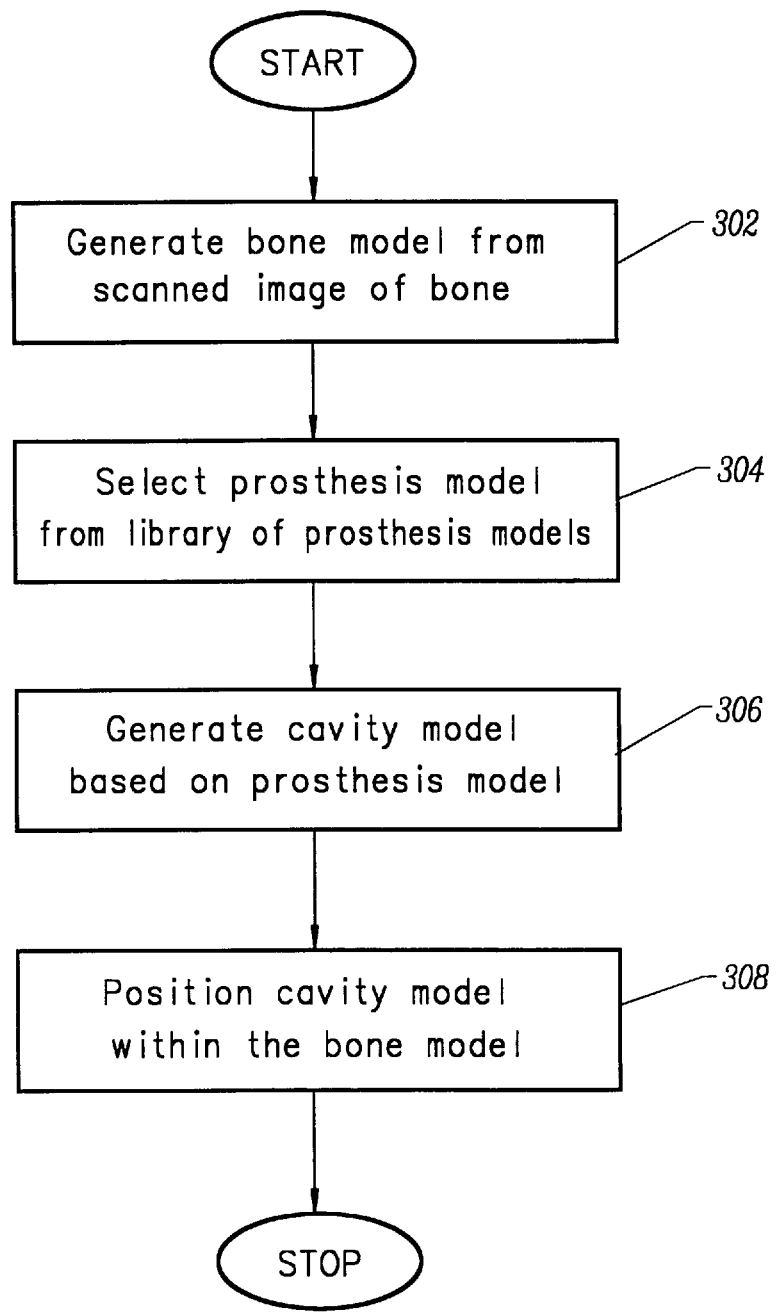
FIG. 6 is a high level flow chart of the method of generating a bone cavity model according to the present invention.

FIG. 6 shows a high level flowchart of the method of planning the position of a prosthesis within a femur bone according to the present invention. More detailed aspects of the present invention will be discussed in reference to the figures that follow. At step 302, the system generates a bone model based on input image data of a patient's femur. The image data may be a CT scan, x-ray, and the like. Utilizing the image data, the system displays multiple views of the femur on the display screen. The surgeon or user selects a prothesis model from a database containing a library of femoral protheses at step 304. Once the prosthesis model is chosen, the user generates a cavity model based on the prothesis model at step 306, and then positions the cavity model within the bone model at step 308. Preferably, the prosthesis and cavity model are pre-generated before the bone mode is created from the CT scan. However, it will be readily recognized that the cavity and prosthesis models can be generated after the bone has been scanned. Exemplary algorithms for these latter two steps are described in detail below.

Once the femoral implant has been selected, and its position within the femur bone determined, robot assisted surgery is performed to implant the new femoral prosthesis. During surgery, the surgeon initially exposes the femur and attaches the robot to the femur. The robot then machines the new cavity to remove the bone cement and prepare for the new implant. After the cavity is machined, the surgeon implants the new femoral prosthesis and closes the incision. A more complete description of this procedure can be found in commonly assigned, co-pending application Ser. Nos. 08/526,826 and 08/606,989 (Attorney Work Dockets 17150-000200 and 17150-000500, respectively), the complete disclosures of which has previously been incorporated herein by reference.

Figure 7:
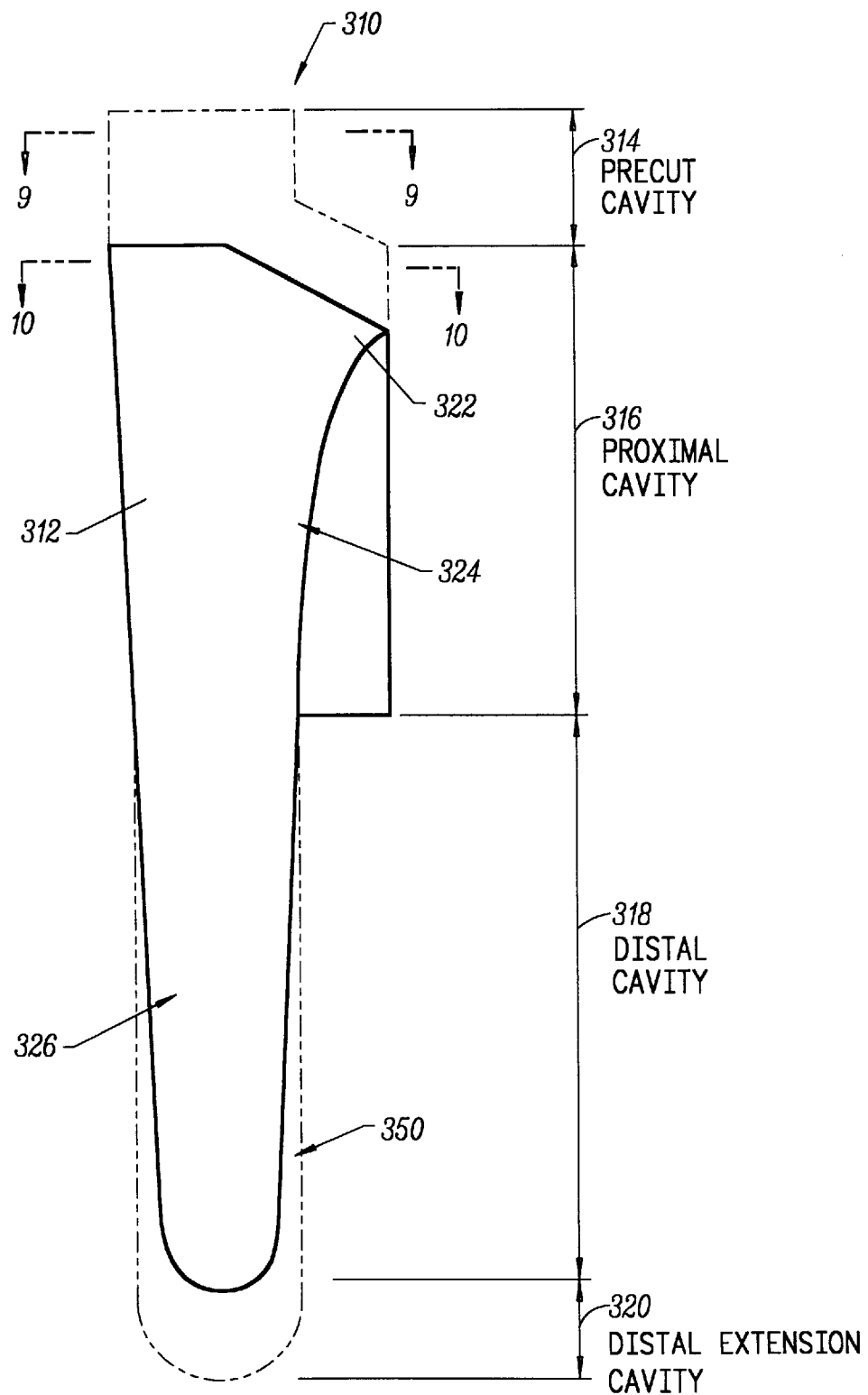
FIG. 7 is a schematic illustration of a cavity model generating according to the method of the present invention.
Figure 8:
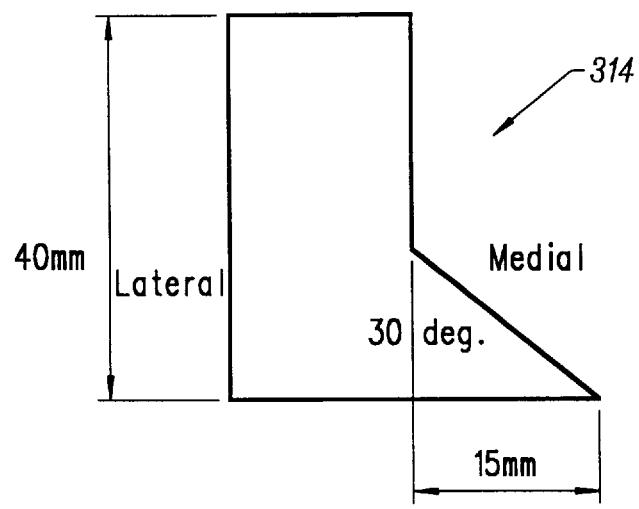
FIG. 8 schematically illustrates an access region or precut cavity of the cavity model of FIG. 7.
Figures 9, 10:
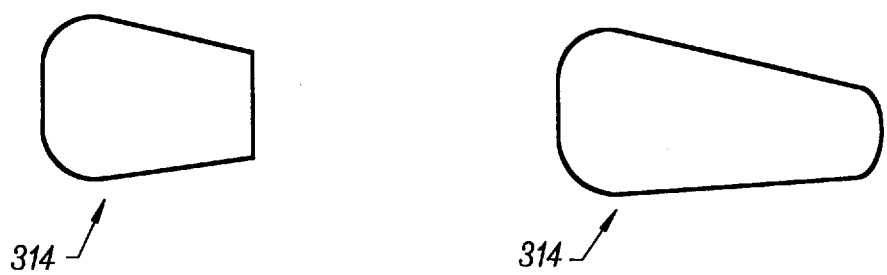
FIGS. 9 and 10 are transverse cross-sections of the cavity model of FIG. 7 taken along lines 9—9 and 10—10, respectively.

With reference to FIGS. 7–12, an exemplary algorithm for generating a cavity model 310 based on a prosthesis model 312 will now be described. In this algorithm, the cavity model 310 is created solely from a prosthesis model, which is a general model that schematically represents a typical prosthesis. In addition to the prosthesis model, the cavity model may be generated from a broach model and/or from the bone model. As shown in FIG. 7, cavity model 310 is generally structured as a composite having at least four different parts: an access region or precut cavity 314, a proximal cavity 316, a distal cavity 318 and a distal extension cavity 320. Precut cavity 314 is a region above the proximal portion of the prosthesis, (when it is located in the bone) that typically must be removed to provide access to the actual cavity in which the prothesis will be implanted. Proximal cavity 316 generally refers to the proximal portion of the cavity that is wider in the lateral/medial direction than the remainder of the cavity to accommodate the head region 322 and the proximal portion 324 of the prothesis model 312. Distal cavity 318 generally refer to the distal portion of the cavity that is more narrow in the lateral/medial direction to accommodate distal portion 326 of the prosthesis model 312 and to provide a relatively tight interference fit with the implant. Distal extension cavity 320 is the portion of the cavity that extends beyond the distal point of the prothesis model 312 to provide room for subsidence of the implant after it has been deployed within the cavity (discussed below).

As shown in FIGS. 7–10, the precut cavity 314 preferably includes a lateral region 328 and a medial region 330. The lateral region 328 will typically have a cross sectional area approximately the same size as the cross sectional area of the distal cavity 318 (i.e., approximately the same cross-sectional area as the mid-section of the prosthesis model 312, see FIG. 9). The medial region 330 will be determined preferably by calculating the cross sectional area of proximal portion 324 of prosthesis model 312 (see FIG. 10) and trimming this cross section based on a recession angle for the implant and a specified distance to which the trimming is to be completed. The recession angle is the angle approximating the angle of the top surface of the bone prior to cutting the cavity. Thus, it should be noted that the region immediately above medial region 330 is air, i.e., this region does not need to be cut. Providing a cavity model 310 with a recession angle minimizes the amount of time spent by the cutter in air, because it emulates the actual osteotomy cut carried out by the surgeon.

Proximal cavity 316 will generally be created from the implant geometry, the broach geometry (in manual procedures) and other clinical parameters including the type of fit appropriate for various regions based on cutter accuracy and based on the clinical requirements of the implants. Typically clinical parameters may include the amount of interference or press fit in the proximal area, the amount of clearance beyond the tip of the implant for subsidence, etc. In one embodiment, an algorithm for determining the proximal cavity involves obtaining implant and broach cross sections at regular intervals and obtaining the proximal cavity cross section based on an "interference pattern" (see FIG. 11). The "interference patterns" generally refers to the portions of the cavity where the implant cross section is larger than the broach cross section. At these portions, the implant will interfere or press against the bone because the broach will cut out a cavity having a smaller cross section than the implant. Surgeons will often desire an interference pattern in portions of the proximal cavity 316 to provide for certain clinical parameters, such as loads between the implant and the bone, a press fit to maintain the position of the implant within the bone and the like.

Figure 11:
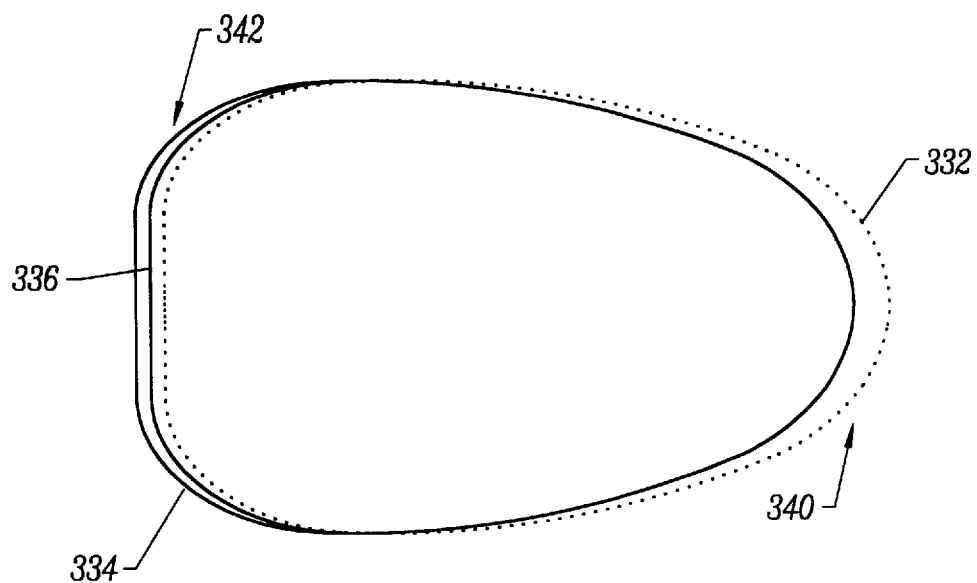
FIG. 11 schematically illustrates a method of generating a proximal cavity region of the cavity model of FIG. 7.

FIG. 11 illustrates an example of implant 334, broach 332 and cavity 336 cross sections at one portion of the proximal cavity 316. As shown, the broach cross section 332 extends further outward than the implant cross section 334 on the medial side 340 of the cavity. On the lateral side 342 of the cavity, however, the implant cross section 334 extends further outward than the broach cross section 332. In an exemplary configuration, the proximal cavity cross section 336 will be offset on the lateral side 342 so that it falls between the broach and implant cross sections 332, 334. This preferably provides a 30% to 70% interference pattern and more preferably a 40% to 50% interference pattern between the broach and implant cross sections 332, 334. On the medial side 340 of the cavity, the cavity cross section 336 will generally be coincident with the implant cross section 334, thereby leaving a gap between the implant and the bone. As shown in FIG. 7, it is often desirable to have an interference pattern on the lateral side 342 of the implant and a gap on the medial side 340 of the implant to accommodate the shape of the implant (i.e., a generally straight lateral side and a tapering medial side).

Figure 12:
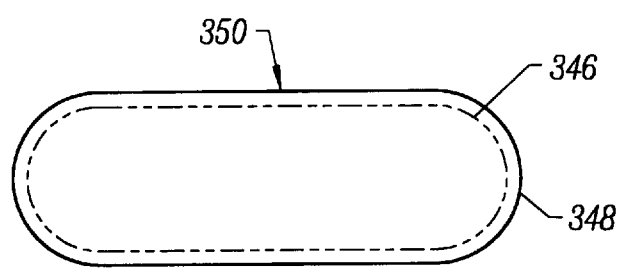
FIG. 12 schematically illustrates an alternative method of generating a proximal cavity region.

FIG. 12 illustrates another example of an exemplary interference pattern for an automatic implant procedure. As shown, the cavity cross section 346 is generally smaller than the implant cross section 348. Preferably, the cavity and implant cross sections 346, 348 will define a substantially even gap 350 around the entire cross-section such that a substantially uniform interference pattern is formed between the implant and the bone. Of course, those skilled in the art will recognize that other types of interference patterns, or no interference pattern at all, may be used to design the cavity model, depending on the clinical parameters of the particular procedure.

Distal cavity 318 will generally be formed in a similar manner as the proximal cavity 316, i.e., by determining an interference pattern between the broach and implant cross-sections. As shown in FIG. 7, the distal cavity 318 will generally have a smaller cross sectional area than the proximal cavity 316 to accommodate the more narrow distal portion 326 of the prosthesis model 312. Since the prosthesis model 312 continues to narrow in the distal direction, distal cavity 316 will define a gap 350 that widens in the distal direction. This gap 350 is often desirable to create a slip fit between the bone and the distal portion of the prosthesis, which provides rotational stability to the prosthesis.

Distal extension cavity 320 is generally created by determining the cross section at the distal end of the distal cavity 318, and extending this cross section by a specified parametric amount. This parametric amount can be determined by a variety of clinical factors. One such factor is the thickness of the cortical bone and the metaphyseal contact between the bone and the implant. For example, if the femur has a generally thick cortical bone and a solid metaphyseal contact with the implant, the surgeon may assume that the implant will not subside by a large distance during its lifetime. Accordingly, it may not be necessary to extend the distal portion of the cavity by a large amount. In the opposite case, if the cortical bone is relatively thin and/or the metaphyseal contact is not as strong, the surgeon may assume that the implant will subside a relatively large distance and the distal extension cavity 320 will be extended to accommodate this subsidence.

Once the cavity model 310 has been completed, this model will be incorporated into the bone model to determine the optimum prosthesis size and shape, and a reasonable initial location for automatic placement of the prosthesis within the bone. Of course, it will be understood that the prosthesis may be manually placed within the bone. Automatic placement of the implant within the bone can be determined by optimizing a variety of factors, such as maximizing the press or interference between certain portions of the implant and the cortical bone, minimizing the amount of cortical bone that is removed to create the cavity, minimizing the gap between the certain portions of the implant and the cortical bone, or ensuring that a maximum press in the cortical bone is not exceeded. A variety of different algorithms can be developed to optimize these and other factors.

Figure 14:
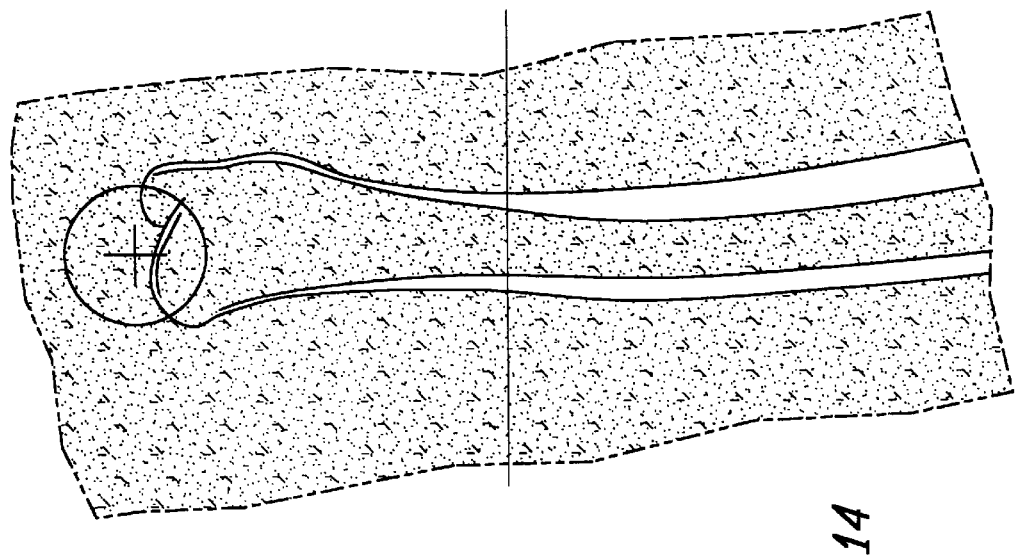
FIGS. 13 and 14 are anterior/posterior and medial/lateral views, respectively, of a scanned image of the femur bone, illustrating a method for determining a medial arc and a distal canal area of the femur bone.
Figure 13:
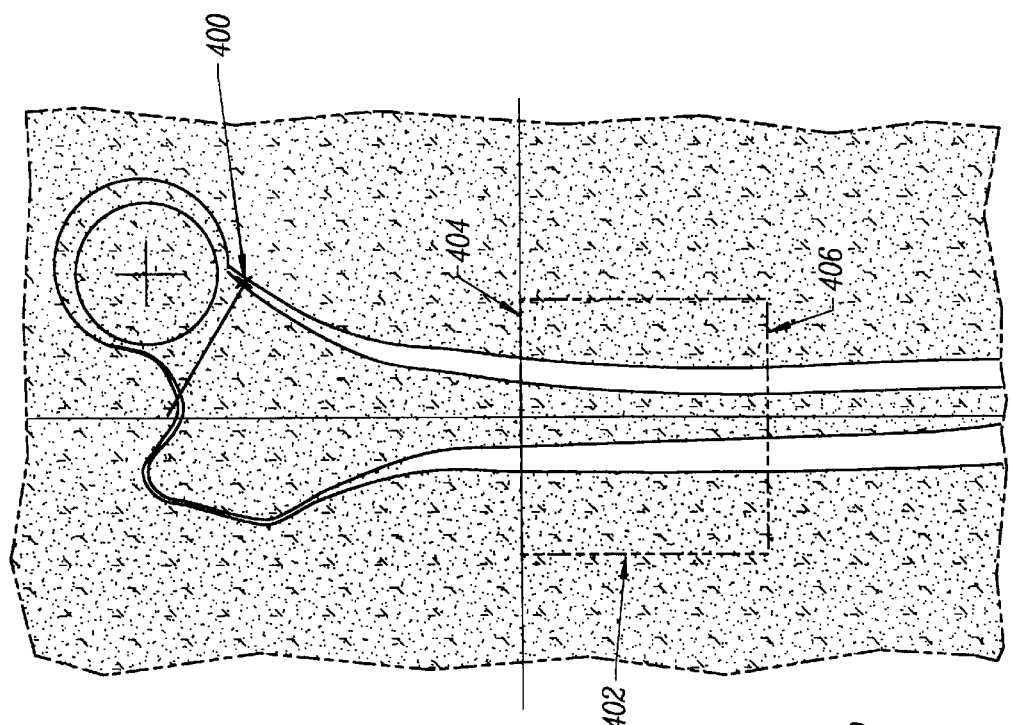

With reference to FIGS. 13–20, an exemplary algorithm for determining the automatic placement of the prosthesis within the bone will now be described. As shown in FIGS. 13 and 14, a bone model based on a scanned image of the patient's femur bone will be presented in anterior/posterior (FIG. 13) and medial/lateral (FIG. 14) views. Preferably, the surgeon will employ the ORTHODOC™ presurgical planning workstation to generate a CT scan of the bone. As shown in FIG. 13, the surgeon interactively marks the top of the medial arc 400 of the cavity, preferably by picking a point where the surgeon wishes to locate the top of the medial arc of the implant. The surgeon may then mark the approximate "distal canal" area 402 of the bone, by marking the top 404 and bottom 406 of the distal canal area 402 perpendicular to the axis of the anterior/posterior view. The distal canal area 402 of the femur is generally the area where the femur appears to be approximately straight.

Figure 15:
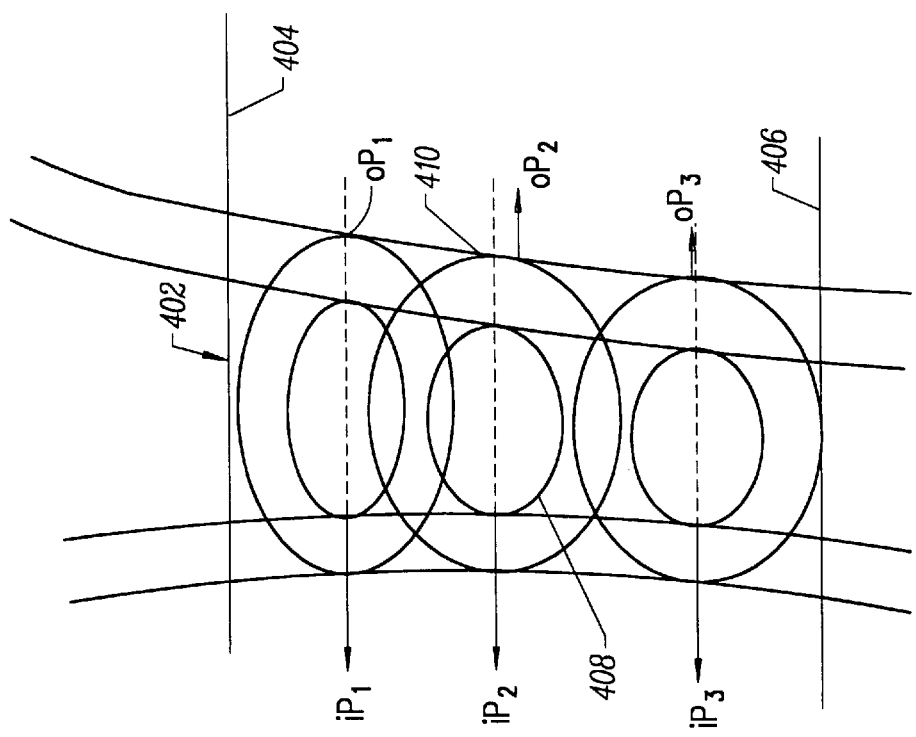
FIG. 15 schematically illustrates a method for determining the inner and outer profiles of the distal canal area of the femur bone.

Referring to FIG. 15, the inner and outer profiles 408, 410 of the distal canal area 402 are then calculated at graduated intervals. The inner and outer profiles 408, 410 may be calculated using a variety of conventional methods. One such method involves determining a threshold value to develop each profile at a particular depth along the canal 402 (i.e., determining the brightest pixel above a threshold brightness in a grey scale image to determine the boundaries of the canal). In another method, a surface model of the inside and outside surface of the femur are developed. Other methods involve performing algorithms, such as the "march and cubes" algorithm, and sectioning the bone model at appropriate depths based on the algorithms.

Figure 16:
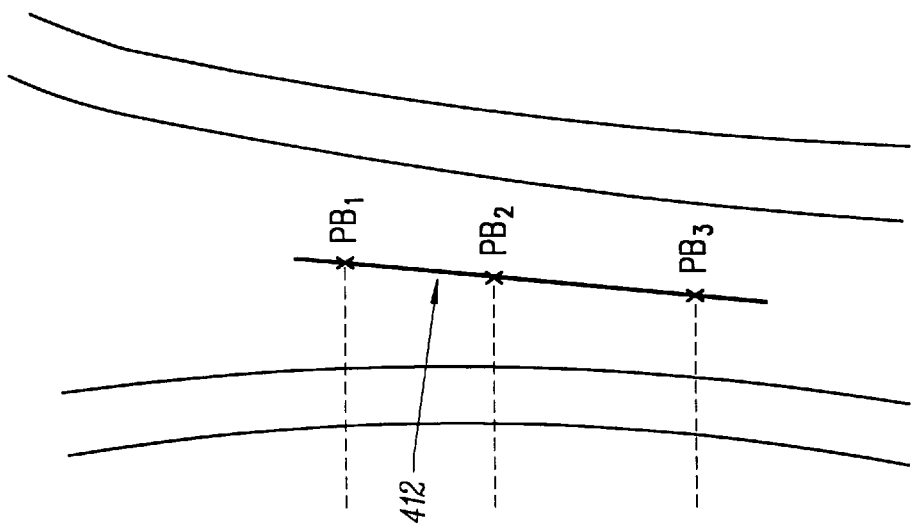
FIG. 16 illustrates a method for determining the barycenter of the inner and outer profiles of FIG. 15.

Once the inner and outer profiles 408, 410 of the distal canal area 402 have been determined, the barycenter 412 of these profiles is calculated, as shown in FIG. 16. The barycenter for any point set is the average of the point set, and for any point set [$P_1, P_2, P_3$ . . . ] is given by:

$$PB(x) = \Sigma_i(x)/n$$

$$PB(y) = \Sigma_i(y)/n$$

Using these points, a line may be fitted using the least squares approximation or other suitable models, through the barycenters found as discussed above. This line is the calculated initial axis for the prosthesis, as shown in FIG. 16.

Figure 18:
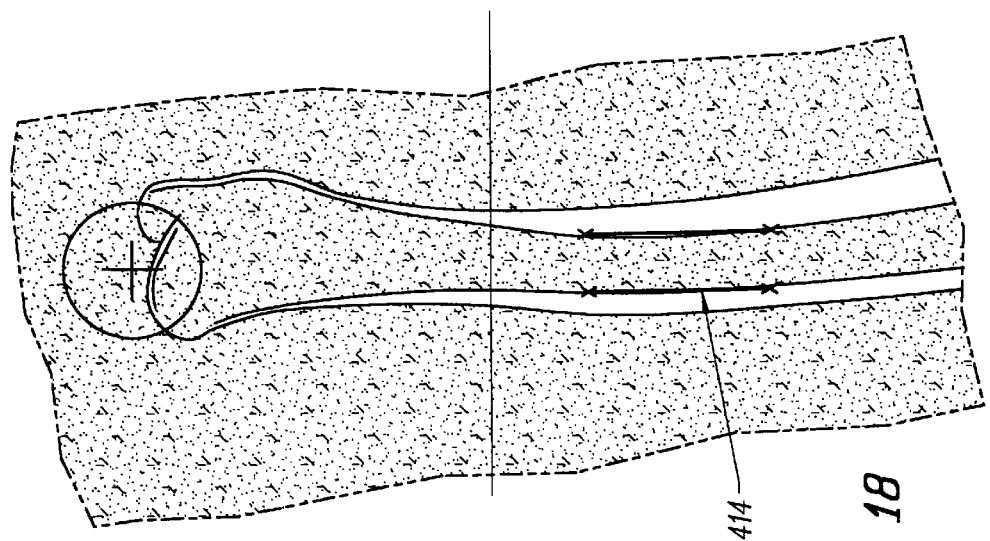
FIGS. 17 and 18 illustrate another method of determining the inner profile of the distal canal area of the femur bone.
Figure 17:
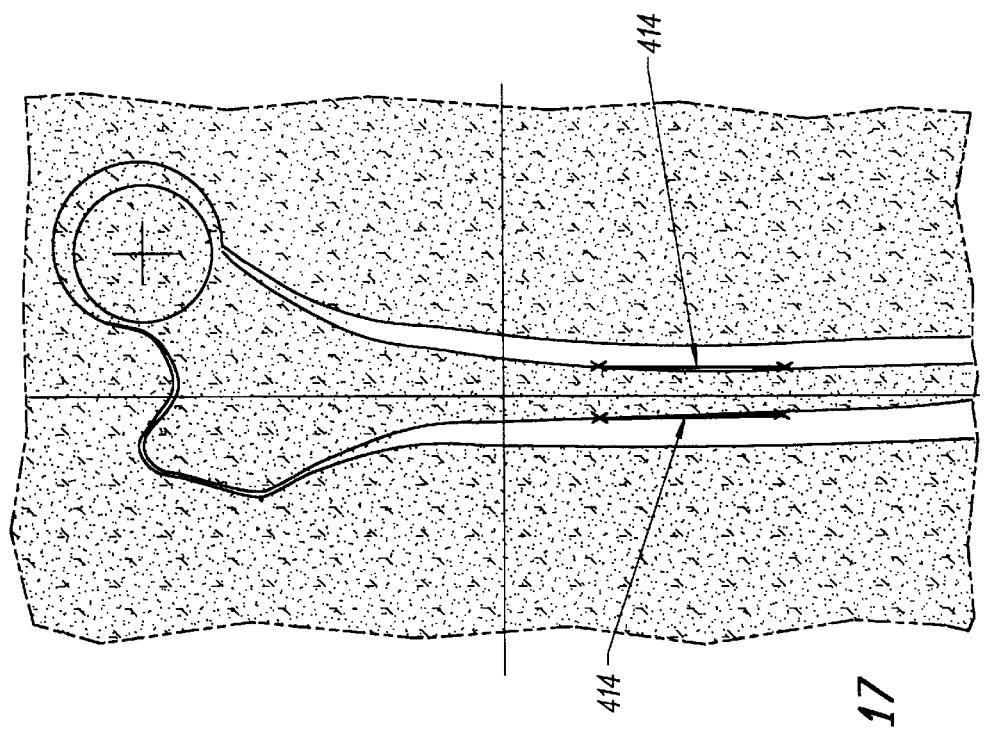

Referring to FIGS. 17 and 18, the inner profile of the femoral canal 414 may then be calculated based on a longitudinal cross-section of the bone. This calculation may be performed in variety of ways, such as using a threshold value to arrive at the inner profile, using a contrast based value to develop the inner profile, or the like. FIGS. 17 and 18 illustrate anterior/posterior and lateral/medial views, respectively, of the inner profile of the entire femoral canal 414.

Once the initial placement for the prosthesis has been determined by the surgeon, an optimal implant size will be determined so that the surgeon may select an optimal prosthesis from the library of available prostheses. The optimal implant size will preferably be based on a fit criteria, which can be a general fit criteria, manufacturer's specified fit criteria, or surgeon determined fit criteria based on a particular femur. The fit criteria will generally include a number of clinical factors that should be optimized. Preferably, each fit criteria will have a weight depending on its relative importance, and an algorithm will be developed based on the fit criteria and their weights to provide an overall quantitative value for each sample prosthesis.

Referring to FIGS. 19–21, an exemplary fit criteria for a model prosthesis will now be described. In this exemplary method, the fit criteria will include minimizing of distal bone cutting $D_1$ (assigned a weight wd1), maximization of distal bone contact $D_2$ (assigned a weight wd2), maximization of proximal contact $P_1$ (assigned a weight wp1) under the condition that a maximum press in the cortical bone is not succeeded and minimization of gaps between the distal surface and the cortical bone $D_3$ (assigned a weight wd3). An algorithm can be formulated for a group of implants to determine a quantitative value for each implant based on the fit criteria and the assigned weights. For example, the algorithm can be set so that the largest (or smallest) quantitative value will be the optimum implant.

Figure 19B:
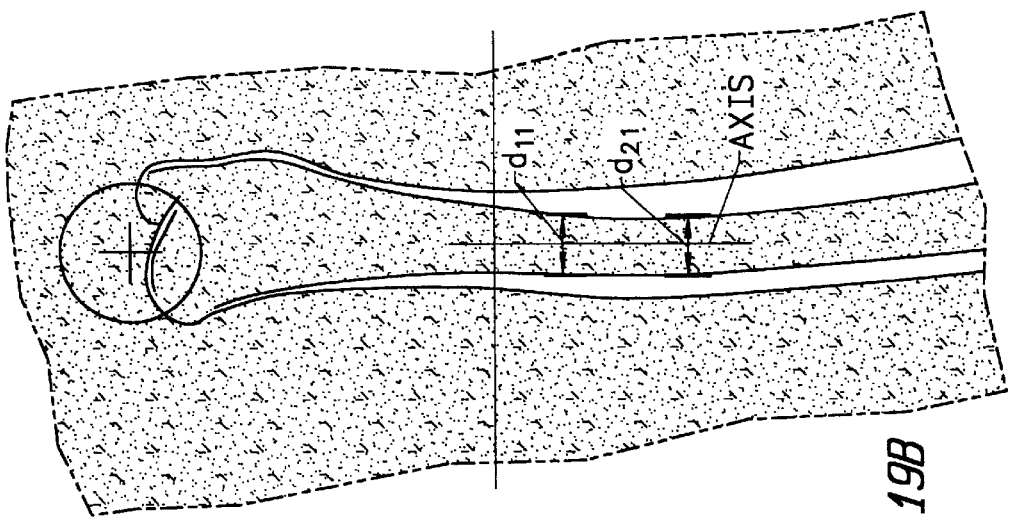
FIGS. 19A and 19B are anterior/posterior and medial/lateral views, respectively, of a scanned image of the femur bone, illustrating a method for determining the minimum and maximum dimensions of the distal canal area of the bone.
Figure 19A:
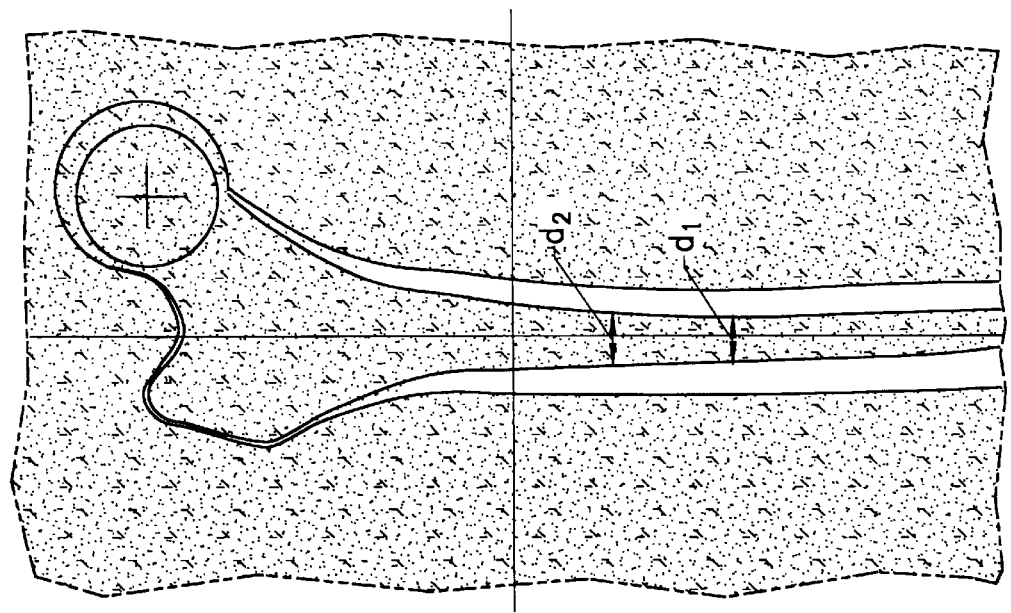

Referring to FIGS. 19A and 19B, the surgeon determines the minimal distal dimensions of each implant within the group by determining the minimum cross-sectional width $d_1$ of the distal canal (FIG. 19A) from the inner profiles 408 calculated above. The maximum distal dimensions of the implant are then selected by finding the minimum distal size $d_{11}$ in which the distal portion of the implant is completely in contact with the cortical bone (FIG. 19B). The maximum and minimum proximal sizes (not shown) for the implant may then be determined in a similar manner. For example, the maximum proximal size is the minimum prosthesis proximal size which exceeds the maximum press requirement. This value can, for example, be found heuristically by calculating the bone press at three or more cross sections. The minimum proximal size may be selected by finding the maximum proximal size for which there is substantially no bone press, or for which the bone press is at a minimum.

Figure 20A:
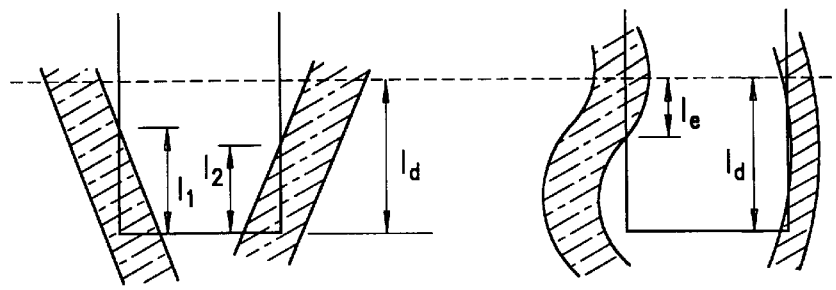
FIGS. 20A–20D illustrate methods of determining fit criteria for a group of implants within the cavity model of FIG. 7.
Figure 20B:
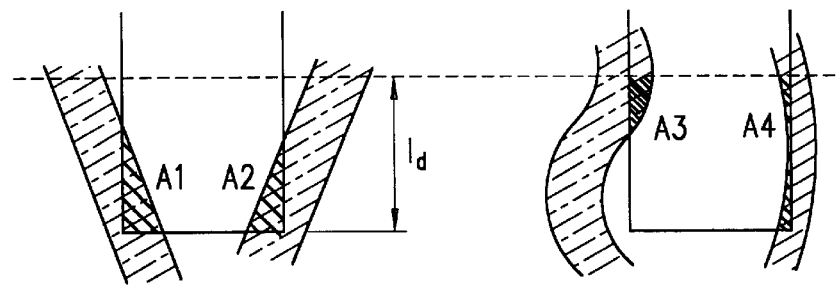

Once the suitable dimensions of the implants have been calculated, the surgeon may then determine a fit criteria for each implant from the anterior/posterior and medial/lateral views. As shown in FIG. 20A, the total distal cortical bone that is removed ($D_1$) for each implant is calculated from both the anterior/posterior and medial/lateral views. The total distal cortical bone cutout $D_1$ is generally equal to the area of cortical bone cutout in both views divided by the maximum area of cortical bone cutout from among the implants in consideration. The area of cortical bone cutout can be determined by computing the cross sectional area of the implant and then determining which areas (A1, A2, A3 and A4) will be cut out in both the anterior/posterior and the medial/lateral views. The total distal contact percentage between the cortical bone and the implant ($D_2$) can be determined by determining the length in contact in both views divided by the total possible length in contact. Thus, as shown in FIG. 20B, the surgeon determines the total length in contact from both views, i.e., $L1+L2+L3+L_d$ and divides this by the total possible length in contact or $4L_d$.

Figure 20C:
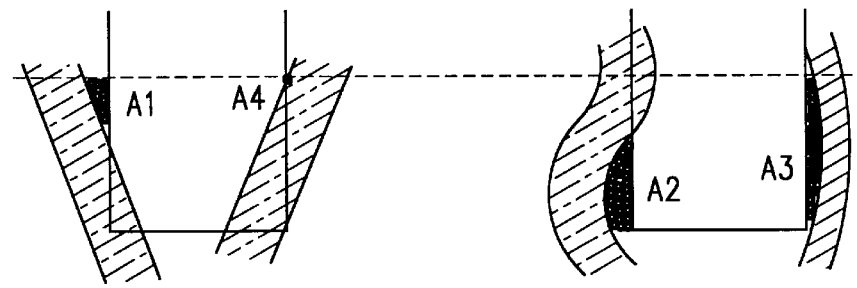
Figure 20D:
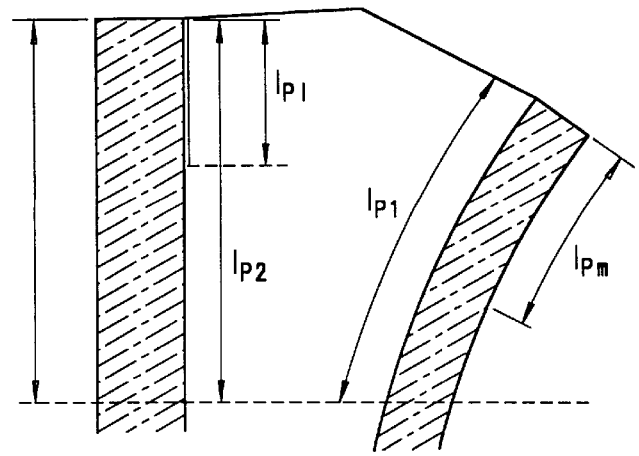

Referring to FIGS. 20C and 20D, the surgeon may then determine the gap percentage $D_3$ between each implant and the bone and total proximal contact $P_1$ for the group of implants. As shown in FIG. 20C, the surgeon determines the gap percentage $D_3$ by estimating the area of gaps in both views (i.e., A1+A2+A3+A4) and dividing this by the maximum gap area from among the implants under consideration. The total proximal cortical contact ($P_1$) can then be determined by computing the length in contact with the cortical bone divided by the total desired length of cortical contact. Thus, as shown in FIG. 20D, the length in contact with the cortical bone is equal to $L_{PL}+L_{PM}$ and the desired contact length is $L_{P1}+L_{P2}$. The total proximal contact as a percentage of maximum possible is $$P_1=(L_{PL}+L_{PM})/(L_{P1}+L_{P2})$$

Once the approximate fit criteria has been determined for the group of implants, a quantitative value can be found by multiplying the fit criteria by the assigned weights. Thus, an example formula for determining the quantitative value is:

$$Q=(1-D_1)*wd_1+D_2*wd_2+(1-D_3)*wd_3+P_1*W_{P1}$$

As can be understood by those in the art, the factors desired to minimize, such as the distal bone cutout ($D_1$) and the gaps between the implant and the cortical bone ($D_3$) are manipulated so that higher values are reflected as lower values in the above formula. On the other hand, the fit criteria that should be maximized, such as the distal bone contact ($D_2$) and the proximal contact ($P_1$), are simply multiplied by the weight factors. In this manner, the implant having the highest quantitative value will be chosen.

Once the initial cavity model has been generated, this model can be adjusted based on the patient's individual requirements. Basically, the dimensions of the first cavity model are adjusted to produce a second cavity model. The second cavity model is then repositioned either automatically (i.e., by an algorithm similar to that described previously for the first cavity model) or interactively by observing images of the bone model and the second cavity model on the display and adjusting the relative positions of the images as they appear on the display.

While the above is a complete description of specific embodiments of the invention, various modifications, alternative constructions, and equivalents may be used. For example, the present invention may also be utilized in other surgical procedures to replace a bone prosthesis as in knee replacement surgery. Therefore, scope of the invention should be determined not with reference to the above description, but instead should be determined with reference to the appended claims along with their full scope of equivalents.

What is claimed is:

1. A method for planning the position of a prosthesis within a bone, said prosthesis having a proximal and a distal portion, said method comprising:
   providing a model of the prosthesis and a model of the bone; and
   generating based on the prosthesis model a first cavity model intended to accommodate the prosthesis within the bone,
   said cavity model comprising an access region, a proximal cavity region, a distal cavity region, and a distal extension region,
   said distal cavity region dimensioned to provide an interference fit between said prosthesis model and said bone, and
   said distal extension region extending beyond the distal end of the prosthesis to provide room for subsidence of the prosthesis within the bone.

2. A method as in claim 1, further comprising positioning the cavity model within the bone model.

3. A method as in claim 2, wherein the positioning step comprises automatically positioning the cavity model within the bone model based on measurements of the bone model and prosthesis fit criteria.

4. A method as in claim 3 wherein the fit criteria include minimizing bone cutting, maximizing bone contact and minimizing gaps between the bone and the prosthesis.

5. A method as in claim 3 further comprising selecting a group of implants and determining a quantitative value for each implant within the group based on the fit criteria.

6. A method as in claim 3 wherein the measurements of the bone model include marking the top of a medial arc portion of the bone model and measuring inner and outer profiles of a distal canal region of the bone model.

7. A method as in claim 2, further comprising cutting the bone to form a cavity having the position and dimensions of the cavity model in the bone model.

8. A method as in claim 7 wherein the bone cutting step comprises generating a file of cutting parameters, transferring the file to automated cutting apparatus, and cutting the bone cavity based on the cutting parameter file.

9. A method as in claim 1, wherein the bone model is generated from a scanned image of the bone.

10. A method as in claim 1, wherein the prosthesis model is selected from a library of prosthesis models corresponding to different types of prostheses.

11. A method as in claim 1, where the first cavity model is generated by a set of rules which generate cavity dimensions based on the prosthesis model in the absence of the bone model.

12. A method as in claim 10 or 11, wherein the first cavity model comprises an actual cavity and an access region, the method further comprising generating an access region model based on the model of the prosthesis to provide access to the actual cavity.

13. A method as in claim 12, wherein the access region model generating step includes determining a cross-sectional area of a proximal portion of the model of the prosthesis and trimming said cross-sectional area based on a recession angle and a lateral trimming distance.

14. The method of claim 13 further comprising generating a distal cavity extension model by determining the cross-sectional area of the distal cavity region and extending the distal cavity region by a distance based on fit criteria, said fit criteria including cortical bone thickness and contact between the cortical bone and the model of the prosthesis.

15. A method as in claim 12, wherein the actual cavity comprises a proximal cavity region, a distal cavity region and a distal cavity extension, the method further comprising providing a model of a broach and generating a proximal cavity region model based on the prosthesis model and the broach model.

16. The method of claim 15 wherein the proximal cavity region model is generated by applying an interference pattern function to the prosthesis and broach models.

17. A method as in claim 1, wherein the first cavity model is generated by a set of rules which generate cavity dimensions based on both implant model information and bone model information.

18. A method as in claim 1, wherein the bone is a long bone taken from a group consisting essentially of the femur, the tibia, the humerus, the ulna and the radius.

19. A method as in claim 1, wherein the positioning step comprises:
observing images of the bone model and the cavity model on a display; and
adjusting the image of the bone model relative to the image of the cavity model as they appear on the display.

20. A method as in claim 19, wherein the images include at least one of the group consisting of 3D images, axial cross-sectional images, and transverse cross-sectional images.

21. A method as in claim 1 further comprising adjusting the dimensions of the first cavity model to produce a second cavity model and repositioning the second cavity model by observing images of the bone model and the second cavity model on the display and adjusting the relative positions of the images as they appear on the display.

22. A method for planning the position of a prosthesis within a bone, said method comprising:
providing a model of the prosthesis and a model of the bone;
generating based on the prosthesis model a first cavity model intended to accommodate the prosthesis within the bone;
wherein the first cavity model comprises an actual cavity and an access region, the method further comprising generating an access region model based on the model of the prosthesis to provide access to the actual cavity; and
wherein the access region model generating step includes determining a cross-sectional area of a proximal portion of the model of the prosthesis and trimming said cross-sectional area based on a recession angle and a lateral trimming distance.

23. A method for planning the position of a prosthesis within a bone, said method comprising:
providing a model of the prosthesis and a model of the bone;
generating based on the prosthesis model a first cavity model intended to accommodate the prosthesis within the bone;
wherein the positioning step comprises automatically positioning the cavity model within the bone model based on measurements of the bone model and prosthesis fit criteria; and
wherein the measurements of the bone model include marking the top of a medial arc portion of the bone model and measuring inner and outer profiles of a distal canal region of the bone model.

24. A method for planning the position of a prosthesis within a bone, said method comprising:
providing a model of the prosthesis and a model of the bone;
generating based on the prosthesis model a first cavity model intended to accommodate the prosthesis within the bone; and
adjusting the dimensions of the first cavity model to produce a second cavity model and repositioning the second cavity model by observing images of the bone model and the second cavity model on the display and adjusting the relative positions of the images as they appear on the display.

25. A method as in any of claims 22 to 24, wherein the prosthesis model is selected from a library of prosthesis models corresponding to different types of prostheses.

26. A method as in any of claims 22 to 24, where the first cavity model is generated by a set of rules which generate cavity dimensions based on the prosthesis model in the absence of the bone model.

27. A method for planning the position of a prosthesis within a bone, said prosthesis having a proximal and a distal portion, said method comprising:
providing a model of the bone;
providing a first cavity model intended to accommodate the prosthesis within the bone, said cavity model comprising an access region, a distal cavity region dimensioned to provide an interference fit between a prosthesis model and the bone, and a distal extension region extending beyond the distal cavity region; and
positioning the cavity model in the bone model.

28. A method as in claim 27, further comprising positioning the cavity model within the bone model.

29. A method as in claim 27, wherein the bone model is generated from a scanned image of the bone.

30. A method as in claim 27, wherein the bone is a long bone taken from a group consisting essentially of the femur, the tibia, the humerus, the ulna and the radius.

* * * * *